US012788870B2

(12) United States Patent
Huk et al.

(10) Patent No.: US 12,788,870 B2
(45) Date of Patent: Nov. 10, 2026

(54) CASSETTE WITH PRESS-FIT FREE-FLOW PREVENTION FOR INFUSION PUMP

(71) Applicant: B. BRAUN MEDICAL INC., Bethlehem, PA (US)

(72) Inventors: Michael Huk, Lehighton, PA (US); Linda Ammermann, Mount Bethel, PA (US); Shawn Zigmont, Easton, PA (US); Michael Janders, Northampton, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 629 days.

(21) Appl. No.: 18/235,654

(22) Filed: Aug. 18, 2023

(65) Prior Publication Data

US 2025/0058040 A1 Feb. 20, 2025

(51) Int. Cl.
*A61M 5/142* (2006.01)

(52) U.S. Cl.
CPC ......... *A61M 5/142* (2013.01); *A61M 2205/12* (2013.01); *A61M 2205/3331* (2013.01)

(58) Field of Classification Search
CPC .............. A61M 5/142; A61M 2205/12; A61M 2205/3331; A61M 5/14228; A61M 5/14232; A61M 39/281; A61M 39/284; A61M 2205/121; A61M 2205/128
See application file for complete search history.

(56) References Cited

U.S. PATENT DOCUMENTS 4,416,595 A 11/1983 Cromie
4,585,441 A 4/1986 Archibald
4,637,817 A 1/1987 Archibald et al.
4,689,043 A 8/1987 Bisha
5,017,192 A 5/1991 Dodge et al.
5,290,239 A 3/1994 Classey et al.
5,445,613 A 8/1995 Orth
5,478,211 A 12/1995 Dominiak et al.
5,482,438 A 1/1996 Anderson et al.
5,658,133 A 8/1997 Anderson et al.
5,673,588 A 10/1997 Raymond
5,904,668 A 5/1999 Hyman et al.
6,629,955 B2 10/2003 Morris et al.
7,611,498 B2 11/2009 Hasler
8,425,470 B2 4/2013 Beck et al.
8,932,032 B2 1/2015 Orr
(Continued)

OTHER PUBLICATIONS

International Search Report and Written Opinion for PCT/US2024/037581 dated Oct. 29, 2024 (Oct. 29, 2024)—10 pages.

*Primary Examiner* — Cris L. Rodriguez
(74) *Attorney, Agent, or Firm* — CM Law; Stephen J. Weed

(57) ABSTRACT

A cassette with free-flow prevention for use with an ambulatory pump. The cassette includes a free-flow prevention device and a housing. The housing is configured to receive the free-flow prevention device through press-fit insertion to facilitate manufacturing. The housing includes an external face, a press plate coupled to the external face, a lever arm retention system to retain the free-flow prevention device, and vertical sidewalls extending from the external face. The housing additionally includes cutouts in the external face adjacent the vertical sidewalls that permit outward bending of the vertical side walls during press-fit insertion of the free-flow prevention device in a direction perpendicular to the press plate.

15 Claims, 13 Drawing Sheets

(56) References Cited

U.S. PATENT DOCUMENTS

| | | | |
|---|---|---|---|
| 10,850,089 | B2 | 12/2020 | Grant et al. |
| 11,202,859 | B2 | 12/2021 | Burnard et al. |
| 2012/0083737 | A1 | 4/2012 | Beck |
| 2013/0267899 | A1 | 10/2013 | Robert et al. |
| 2014/0219843 | A1 | 8/2014 | Koyama et al. |
| 2019/0099552 | A1 | 4/2019 | Zhang et al. |
| 2021/0146044 | A1 | 5/2021 | Burnard et al. |
| 2021/0170096 | A1 | 6/2021 | Buxton et al. |

CASSETTE WITH PRESS-FIT FREE-FLOW PREVENTION FOR INFUSION PUMP

FIELD OF THE INVENTION

The present disclosure is related to infusion pumps and, more particularly, to a cassette for use with an infusion pump that includes a press-fit free-flow prevention device.

BACKGROUND

Infusion pumps deliver controlled doses of fluids such as medications, analgesics, and nutrition to patients. Infusion pumps are particularly well suited to delivering controlled doses of fluids over long periods of time, e.g., several hours or days. While many infusion pumps are designed for bedside use, there are ambulatory versions available. Ambulatory infusion pumps allow a patient to move around while the infusion pump is in use. This is beneficial for patients who would otherwise be confined to a bed, and it can help patients get some light exercise by walking or stretching. This also allows fluids to be delivered while patients are being transferred.

There are two conventional types of infusion pumps, syringe pumps that depress a syringe to deliver fluid from the syringe to a patient, and peristaltic pumps that act on a tube to control the rate of fluid flow through the tube from a bottle or bag of fluid to a patient. A concern with peristaltic pumps utilizing tubing is that the force of gravity may cause an unintentional flow of fluid from the bottle or bag of fluid through the tube to the patient when the peristaltic pump is not engaged with the tube, which is commonly referred to as free-flow.

SUMMARY

Examples described herein are directed to a cassette for use with an ambulatory pump. The cassette includes a free-flow prevention device and a housing. The housing is configured to receive the free-flow prevention device through press-fit insertion to facilitate manufacturing. The free-flow prevention device includes a clamping section having a first side and a second side, a first elongate section extending from the first side, and a second elongate section extending from the second side (forming a U-shaped clamp). The housing supports the free-flow prevention device and defines a channel for receiving a tube. The elongate sections extend parallel to the channel and the clamping section extends across the channel.

The housing includes an external face, a press plate coupled to the external face, a lever arm retention system configured to retain the free-flow prevention device when received, the lever arm retention system including a first lever arm configured to engage the first elongate section and a second lever arm configured to engage the second elongate section, and vertical sidewalls extending from the external face. Other structures, such as ramps on the vertical sidewalls, may be configured and positioned within the cassette to engage and retain the elongate sections. The vertical sidewalls include a first vertical sidewall spaced from the first lever arm and a second vertical sidewall spaced from the second lever arm. The housing additionally includes cutouts in the external face adjacent the first and second vertical sidewalls and the first and second lever arms that permit outward bending of the first and second vertical side walls and potentially inward bending of the first and second lever arms during press-fit insertion of the free-flow prevention device in a direction perpendicular to the press plate.

BRIEF DESCRIPTION OF THE DRAWINGS

The drawing figures depict multiple views of one or more implementations, by way of example only, not by way of limitations. In the figures, like reference numerals refer to the same or similar elements. The same numeral is used to represent the same or similar element across the multiple views. If multiple elements of the same or similar type are present, a letter may be used to distinguish between the multiple elements. When the multiple elements are referred to collectively or a non-specific one of the multiple elements is being referenced, the letter designation may be dropped.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Figure 1A:
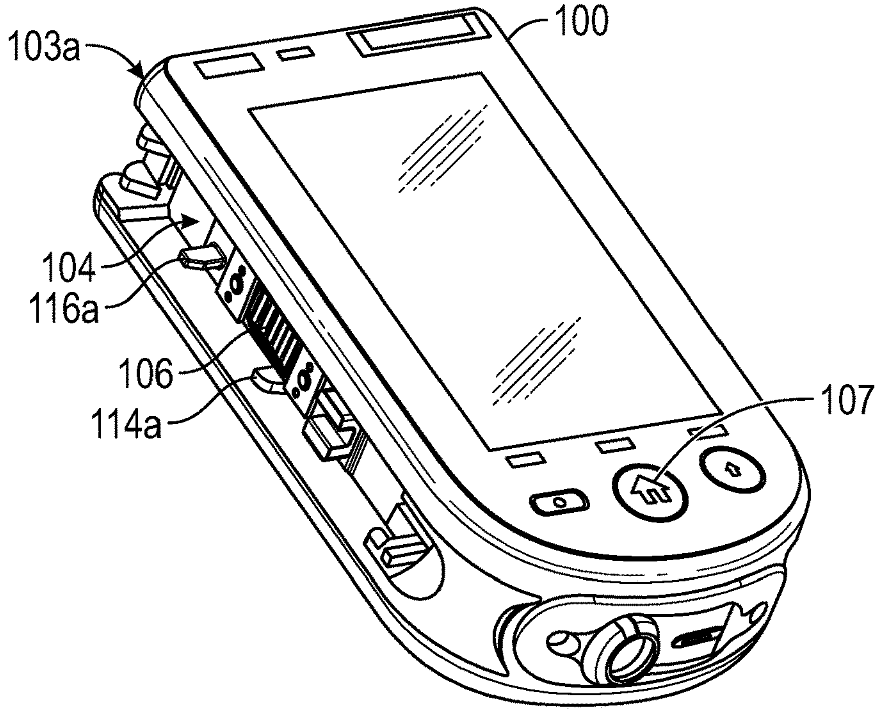
FIG. 1A is a perspective view of an example ambulatory infusion pump.
Figure 1B:
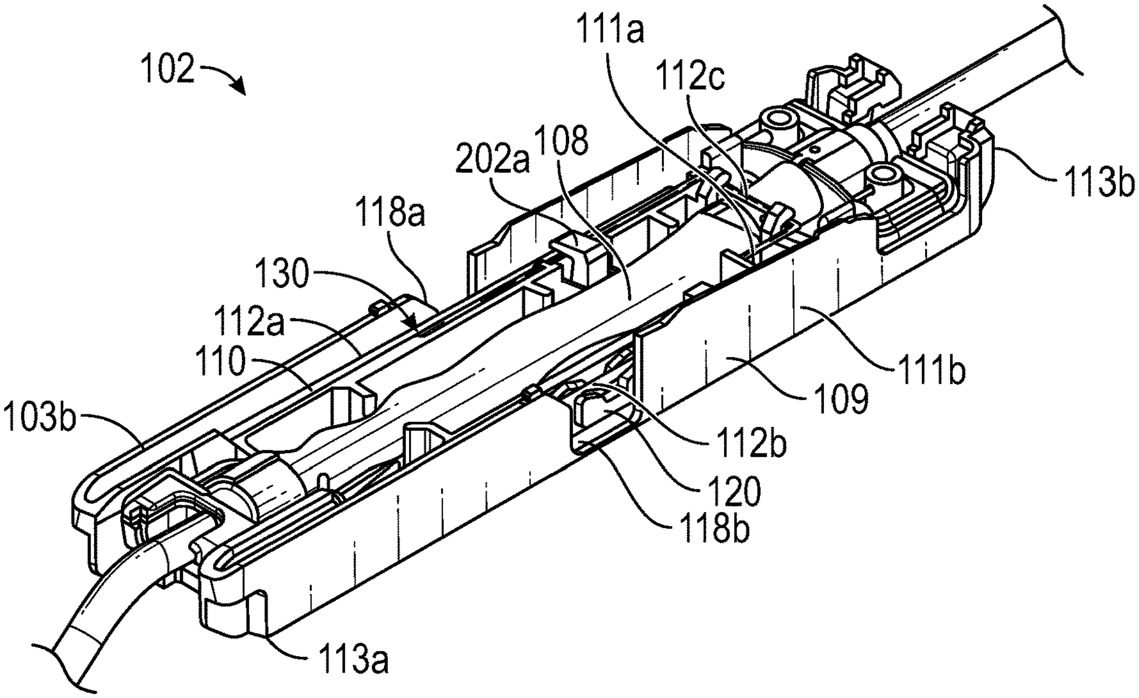
FIG. 1B is a perspective view of an example cassette with a free-flow prevention clamp for use with the ambulatory pump of FIG. 1A.

FIG. 1A depicts an example ambulatory pump 100 and FIG. 1B depicts an example cassette 102 with free-flow prevention for use with the ambulatory pump 100. The ambulatory pump 100 includes a receptacle 104 configured to receive the cassette 102. A peristaltic pump 106 within the receptacle 104 acts upon a tube 108 extending through a channel 424 (FIG. 4B) within the cassette 102 to pump fluid from a fluid container (e.g., a bag or a bottle; not shown) into a patient. Channel walls (e.g., channel wall 130) within the cassette 102 partially define the channel 424. In one example, the channel walls 130 may include breaks or cutouts as illustrated in FIG. 1B (e.g., for lever arms 202*a*, 202*b*; described in further detail below). In other examples, the channel walls 130 may be continuous as illustrated in FIG. 1D (with, for example, the lever arms 202*a*, 202*b* integrated into the side walls 130).

An example free-flow prevention device 110 is positioned within the cassette 102 to allow fluid flow through the tube 108 when the cassette is coupled to the ambulatory pump 100 within the receptacle 104. When the cassette 102 is coupled to the pump, the pump 100 raises the free-flow prevention device 110 and the peristaltic pump 106 controls fluid flow through the tube 108. When the cassette 102 is subsequently disengaged from the pump, the free-flow prevention device 110 cuts off fluid flow through the tube 108 in order to prevent unintentional fluid flow through the tube (e.g., free-flow).

The ambulatory pump 100 includes a user interface for interacting with the ambulatory pump 100. The illustrated user interface includes a display (which may be a touchscreen) and buttons 107. A user controls operation of the ambulatory pump via the user interface. The pump 100 additionally includes a housing 103*a* containing and supporting the components of the ambulatory pump 100 such as the peristaltic pump 106, electronics, and power supplies.

Figure 2A:
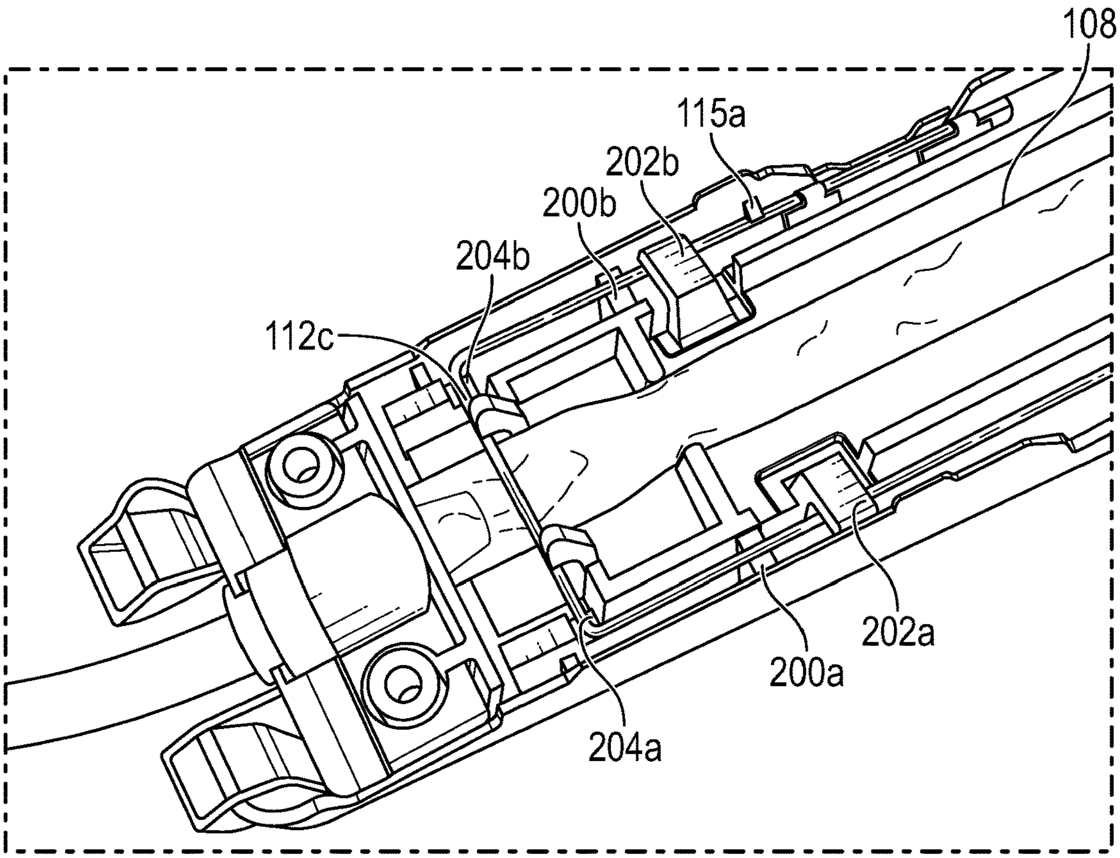
FIG. 2A is a partial perspective view of the cassette of FIG. 1B illustrating the free-flow prevention device in an open, pre-operational state (e.g., shipped state).

The free-flow prevention device 110 includes a first elongate section 112*a*, a second elongate section 112*b*, and a clamping section 112*c* (forming a U-shaped clamp). The housing 103*b* of the cassette 102 supports the free-flow prevention device 110. The housing includes multiple lower supports (e.g., override fulcrums 200*a* and 200*b*; FIG. 2A). The clamping section 112*c* is positioned within the cassette geometry such that, when the cassette 102 is received within the receptacle 104 of the ambulatory pump 100, the clamping section 112*c* extends across the channel receiving the tube 108. The housing of the cassette 102 may be rigid plastic or other material capable of supporting the tube 108 and free-flow prevention device 110.

The first elongate section 112*a* extends from a first side of the clamping section 112*c* and along a first side of the cassette 102 parallel to the channel within the cassette 102 receiving the tube 108. The second elongate section 112*b* extends from a second side of the clamping section 112*c* and along a second side of the cassette 102 parallel to the channel receiving the tube 108. In the illustrated example, the free-flow prevention device 110 is a staple-shaped leaf spring consisting of single piece of metal (e.g., spring steel). In other examples, the free-flow prevention device 110 may be formed in pieces and/or of different materials (e.g., the elongate sections 112*a, b* may be metal and the clamping section 112*c* may be rigid plastic).

The ambulatory pump 100 also includes a pair of arc cams (a first arc cam 114*a* on one side of the receptacle is illustrated FIG. 1A, with the second hidden from view) for engaging the elongate sections 112*a, b* of the free-flow prevention device in order to lift the clamping section 112*c*. Additionally, the ambulatory pump 100 includes a pair of wedge cams (a first wedge cam 116*a* on one side of the receptacle 104 is illustrated FIG. 1A, with the second hidden from view) for transitioning the free-flow prevention device 110 from an open, manufactured/shipped state to an operational state, which is described in further detail below.

The cassette 102 also includes a first cutout 118*a* in a vertical sidewall 109 of the cassette 102 and a second cutout 118*b* in an opposite sidewall of the cassette 102. Additionally, the cassette 102 includes a touch pad 120 positioned on an elongate section 112*b* adjacent a midpoint of the elongate section 112*b* and the cutout 118*b*. The touch pad 120 and cutout 118*b* facilitates engagement of the second elongate section 112*b* by a finger of an operator in order to manually lift the clamping section 112*c* to allow fluid flow through the tube 108 (e.g., for priming the cassette 102) when the cassette 102 is not received within the receptacle 104 of the ambulatory pump 100. The touch pad 120 may be a press-fit piece of rigid plastic. Although the touch pad 120 is illustrated as only on one elongate section 112*b*, a touch pad may also be provided on the other elongate section 112*a*. Additionally, the touch pad 120 may be omitted and an operator may engage the elongate sections 112*a, b* directly to manually lift the clamping section 112*c*.

Figure 1C:
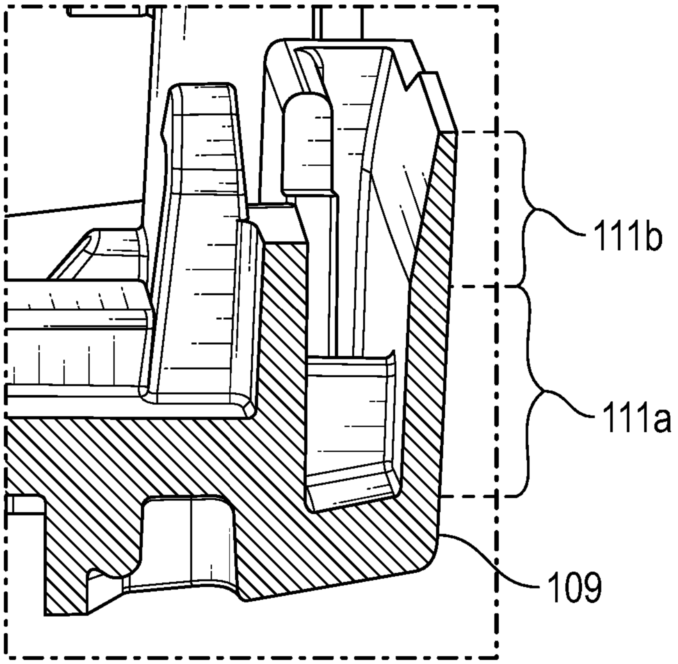
FIG. 1C is a cutaway perspective view illustrating a cross-section of the sidewall of the cassette of FIG. 1B.
Figure 1D:
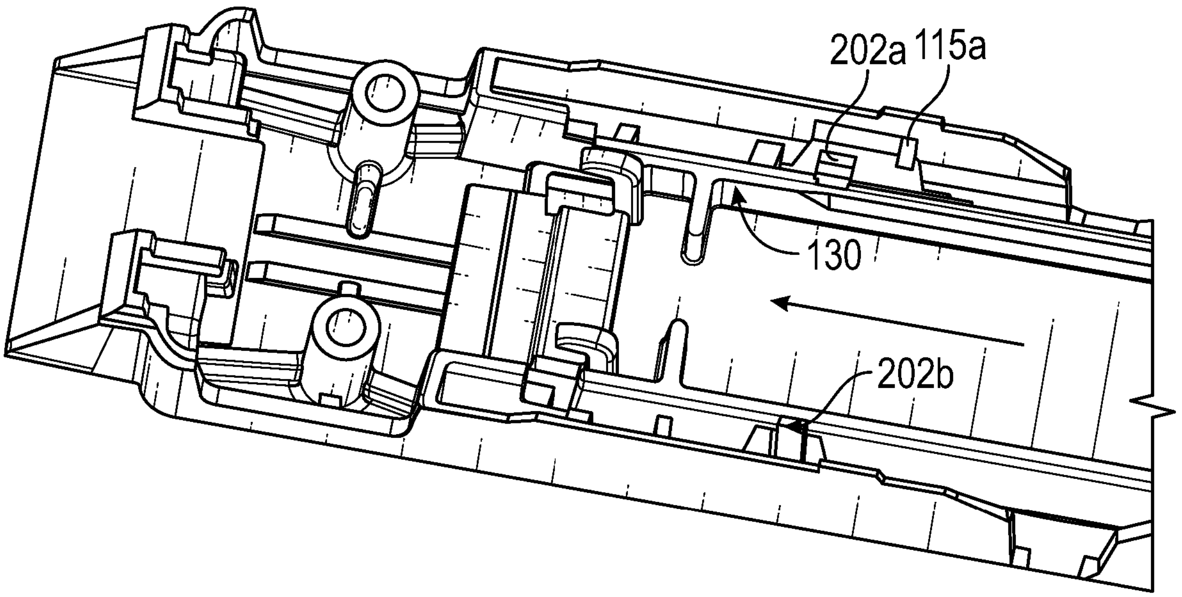
FIG. 1D is a cutaway perspective view illustrating a portion of another example cassette for use with the ambulatory pump of FIG. 1A.

As illustrated in FIG. 1C, the vertical side walls 109 include a first region 111*a* of substantially uniform thickness (e.g., 1.0 mm) and a second region 111*b* that is chamfered (e.g., narrowing from 1.0 mm proximate the first region 111*a* to 0.48 mm near an edge of the cassette 102). The first and second regions 111 of the sidewalls 109 are configured to allow outward bending of the respective sidewall during insertion of the free-flow prevention device 110 to facilitate manufacturing.

FIG. 2A depicts the cassette 102 with the free-flow prevention device 110 in an open, pre-operational state (e.g., manufactured/shipped state). The cassette 102 includes a first ledge 204*a* adjacent a first side of the clamping section 112*c* on one side of the channel receiving the tube 108 and a second ledge 204*b* adjacent a second side of the clamping section 112*a* on an opposite side of the channel receiving the tube 108. The ledges 204*a, b* support the clamping section 112*c* and oppose the downward force being applied to the clamping section 112*c* by the first and second elongate sections 112*a, b*. This prevents the clamping section 112*c* from occluding the tube 108 (e.g., for Ethylene Oxide, EtO, sterilization and/or priming) prior to insertion of the cassette 102 into the ambulatory pump 100.

The housing of the cassette 102 additionally includes a pair of override fulcrums 200*a, b* positioned below respective elongate sections 112*a, b* of the free-flow prevention device 110 and a pair of lever arms 202*a, b* forming a lever arm retention system positioned above respective elongate sections 112*a, b* of the free-flow prevention device 110. The override fulcrums 200*a, b* are positioned between a midpoint of the first and second elongate sections 112*a, b* and the clamping section 112*c*. The lever arms 202*a, b* are positioned between the midpoint of the first and second elongate sections 112*a, b* and the override fulcrums 200*a*. The housing may include addition structures such as a ramp(s) 115*a* on the vertical sidewalls, which may be configured and positioned within the cassette to engage and retain the elongate sections.

After the free-flow prevention device 110 is moved off the ledges 204 and into an operational state, applying a force to the midpoints of the first and second elongate sections 112*a, b* (e.g., by the arc cams 114*a, b* upon attachment of the cassette 102 to the receptacle 104 of the ambulatory pump or by a user's finger) pivots the elongate sections 112*a*, 112*b* about the override fulcrums 200*a, b* to raise the clamping section 112*c* and allow fluid flow through the tube 108. Removing the force while in this state (e.g., by detaching the cassette or withdrawing the user's finger) shifts the pivot to occlusion fulcrums on the lower side of the lever arms 202*a, b*, which lowers the clamping section 112*c* and blocks fluid flow through the tube 108.

Figure 2B:
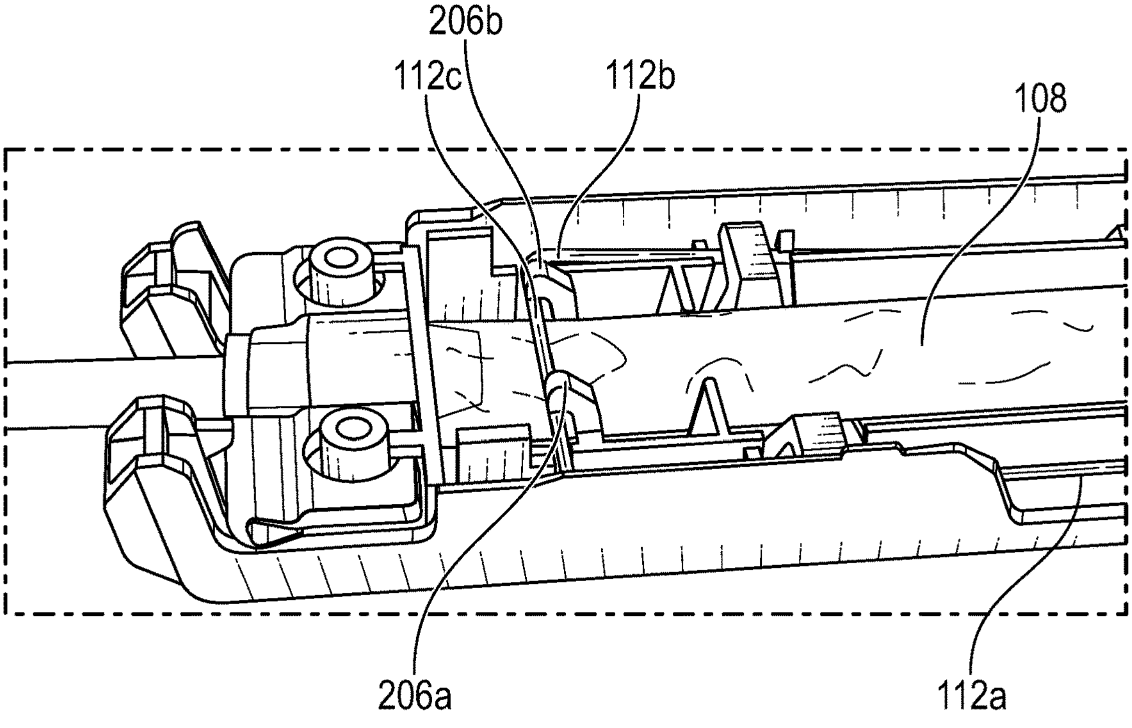
FIG. 2B is a partial perspective view of the cassette of FIG. 1B illustrating the free-flow prevention device in a closed, post-operational state.
Figure 2C:
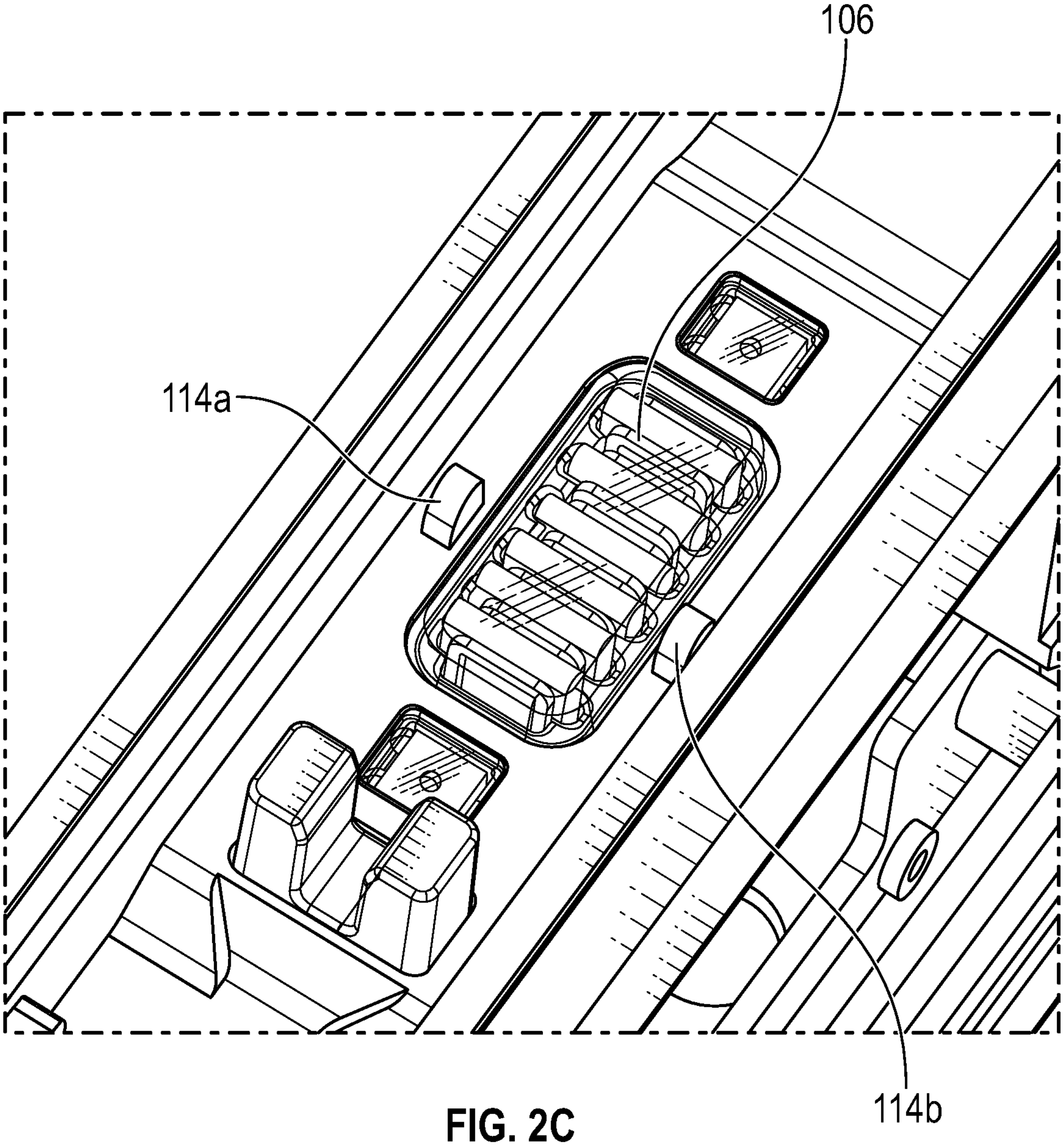
FIG. 2C is a partial perspective view of the pump of FIG. 1A illustrating arc cams that engage the free-flow prevention device when the cassette is coupled to the pump.
Figure 2D:
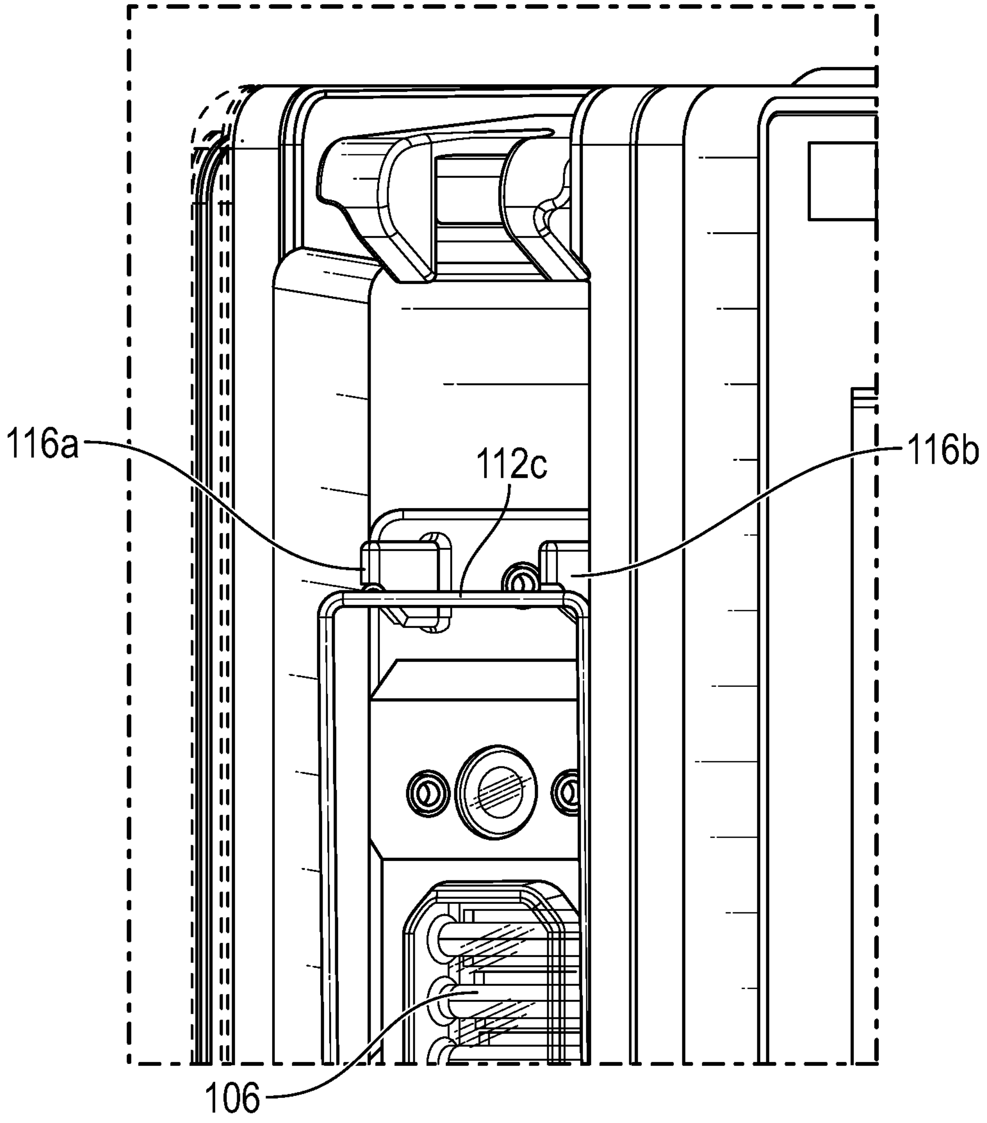
FIG. 2D is a partial perspective view of the pump of FIG. 1A illustrating wedge cams that engage the free-flow prevention device to shift the free-flow prevention device from a shipped state to an operational state when the cassette is coupled to the pump.

FIG. 2B depicts the cassette 102 with the free-flow prevention device 110 in a closed, operational state and FIG. 2C depicts the arc cams 114 and peristaltic pump 106 of the ambulatory pump 100. Positioning hooks 206*a, b* are provided to facilitate placement of the clamping section 112*c* of the free-flow prevention device 110 onto the ledges 204, which maintains the tube 108 in an open condition. FIG. 2D depicts the wedge cams 116*a, b* and their relationship to the free-flow prevention device when the cassette (not shown in FIG. 2D) is attached to the ambulatory pump 100.

The free-flow prevention device 110 is moved off the ledges 204 and out of the open, pre-operational state by the wedge cams 116 as the cassette 102 is attached to the receptacle 104 of the ambulatory pump 100. To attach the cassette 102 to the receptacle 104, a user first inserts an end 113*a* of the cassette 102 into the receptacle 104 near a bottom of the ambulatory pump 100 (also referred to as a toe-in). The user then pushes the opposite end 113*b* of the cassette 102 downward such that the cassette 102 rotates about the toe-in into full engagement with the ambulatory pump 100. As the cassette 102 is rotated into position, the arc cams 114 engage the elongate sections 112*a, b* to apply a force that raises the clamping section 112*c* and angled portions of the wedge cams 116 substantially simultaneously engage the clamping section 112*c* to shift the free-flow prevention device 110 away from the ledges 204. In this manner, the tube 108 remains unobstructed by the clamping section 112*c* when the cassette 102 is attached to the ambulatory pump 100, allowing the peristaltic pump 106 to control fluid flow through the tube 108. In an example, once the free-flow prevention device 110 is shifted from the shipped/pre-operational state into the operational state by the wedge cams 116, the free-flow prevention device 110 remains in the operational state.

Removal of the cassette 102 from the receptacle 104 is accomplished by reversing the process. As the cassette 102 is rotated out of engagement with the ambulatory pump 100, the arc cams 114 disengage from the elongate sections 112*a, b*. With the force from the arc cams 114 removed, and the ledges 204 no longer positioned under the clamping section 112*c* due to the shift of the free-flow clamp 110 during the insertion of the cassette 102, the clamping section 112 rotates downward about the occlusion fulcrums on the lower side of the lever arms 202*a* to close off the tube 108 as depicted in FIG. 2B.

Figure 3A:
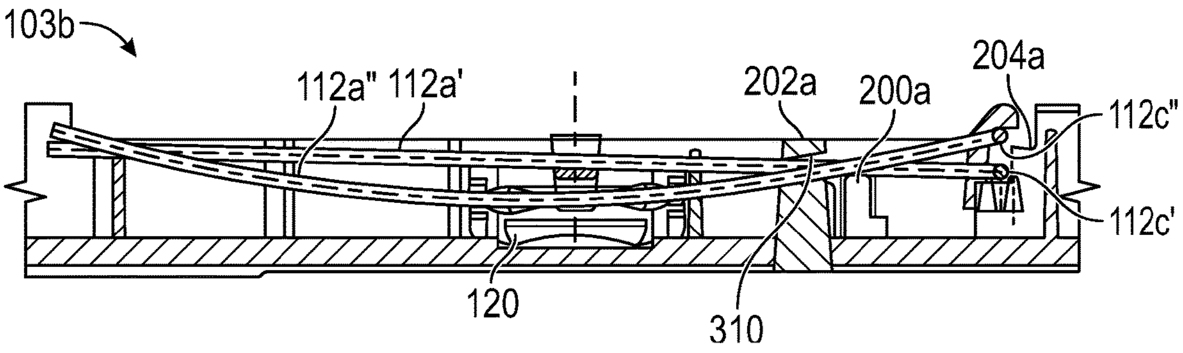
FIG. 3A is a partial side view of the example cassette of FIG. 1B depicting the free-flow prevention device in an open condition and a closed condition.

FIG. 3A depicts movement of an elongate section 112 after shifting the free-flow prevention device 110 off the ledge 204*a* from the open, pre-operational state into the operational state. In the operational state, the first elongate section 112*a* can be in a closed condition (represented by first elongate section 112*a*') or an open condition (represented by first elongate section 112*a*"). In the closed condition, no force is applied to the midpoint of the first elongate section 112', resulting in the clamping section 112*c* rotating downward about an occlusion fulcrum 310 on the lower surface of the lever arm 202*a* to close off the tube 108. In the open condition, force is applied to the midpoint of the first elongate section 112", resulting in the clamping section 112*c* rotating upward about the override fulcrum 200*a* to open the tube 108.

FIG. 3A additionally depicts movement of the touch pad 120 responsive to force applied at the midpoint of the first elongate section 112. In the absence of applied force, touch pad 120 is in a closed position that maintains clamping section 112*c*' clamped against the tube 108. When force is applied (e.g., by an arc cam 114*a* or a user's finger), touch pad 120 is in an open position that raises clamping section 112*c*" to permit fluid flow through the tube 108.

Figure 3B:
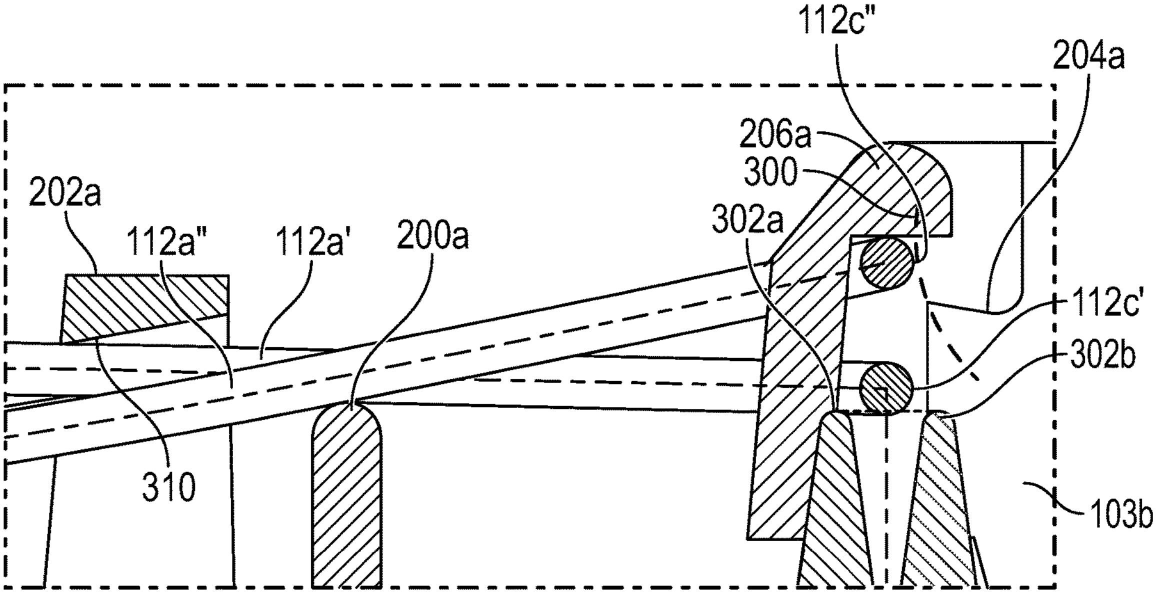
FIG. 3B is a partial side view of the example cassette of FIG. 1B illustrating features of the cassette for configuring the free-flow prevention device in an open pre-operational state, an open operational state, and a closed post-operational state.

FIG. 3B depicts geometry of a portion of the housing 103*b* of the cassette 102 that supports the free-flow clamp 110. Shifting of the clamping section 112*c* of the free-flow clamp 110 is represented by dashed wedge cam shift line 300. Occlusion fulcrum 310 on lower surface of lever arm 202*a* acts on elongate section 112*a*' forcing clamping section 112*c*' downward to occlude the tube 108. In the illustrated example, occlusion ribs 302*a* and 302*b* are positioned perpendicular to the channel receiving the tube 108 and on either side of the clamping section 112*c* to assist with complete closure of the tube 108 when the clamping section 112*c* is in the closed condition. In an alternative example, the occlusion ribs 302*a* and 302*b* are replaced by a single flat section wherein the tube 108 is positioned between the clamping section 112*c* and the flat section. Override fulcrum 200*a* acts on elongate section 112*a*" forcing clamping section 112*c*" upward to enable fluid flow through the tube 108.

Examples of the free-flow prevention device 110 enable the cassette 102 to maintain the clamping section 112*c* in an un-occluded/open state prior to a first attachment of the cassette to the receptacle, maintain the clamping section in the un-occluded/open state upon the first attachment of the cassette to the receptacle, and transition the clamping section to an occluded/closed state upon detachment of the cassette from the receptacle. Additionally, examples of the free-flow prevention device 110 enable the cassette to manually transition the clamping section to an un-occluded state after detachment of the cassette from the receptacle and/or transition the clamping section to the un-occluded state upon subsequent attachments of the cassette to the receptacle.

Figure 4A:
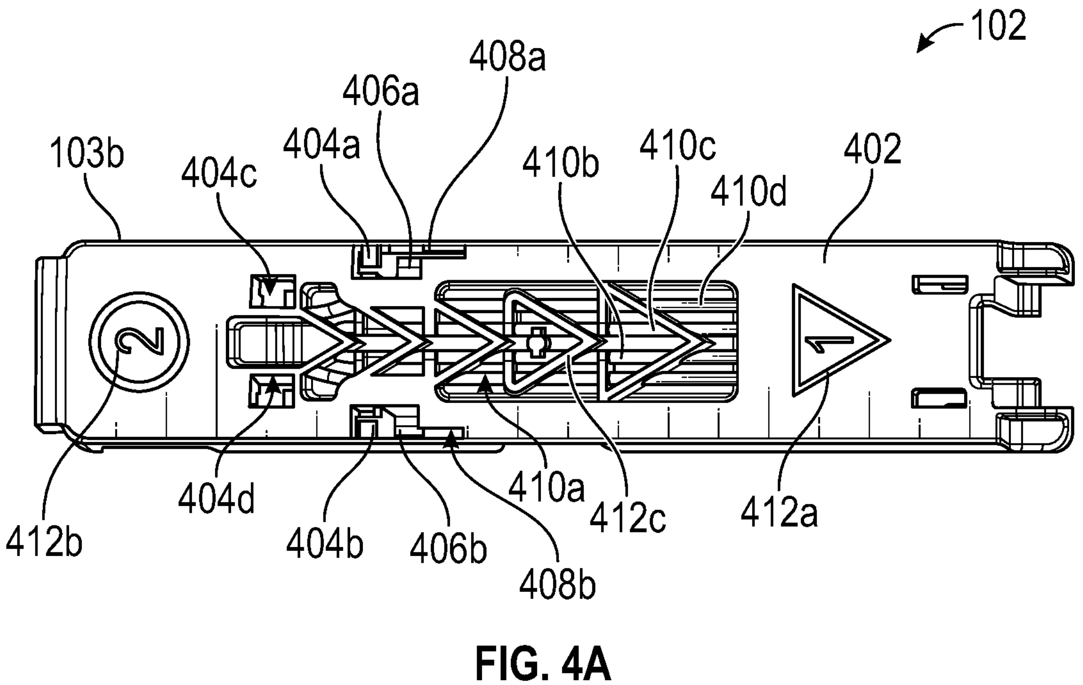
FIG. 4A is a top view of a cassette configured to receive a free-flow prevention device.

FIG. 4A depicts a top view of a cassette housing 103*b* (i.e., the surface facing away from the pump 100 when inserted). The housing 103*b* includes an external face 402 that faces away from the ambulatory pump 100 when the cassette 102 is inserted into the ambulatory pump 100. The external face 402 includes multiple cutouts 404, multiple ribs (4 ribs 410*a-d*) for maintaining rigidity of the press plate 422 (FIG. 4B), insertion indicia 412*a* and 412*b*, and flow direction indicia 412*c*. The insertion indicia 412 includes a first insertion indicia 412*a* (the numeral "1" in a triangle indicating a first step of insertion; e.g., toe-in of one end of the cassette 102 within the pump 100; and also indicating direction of insertion, which matches flow direction in this implementation) and a second insertion indicia 412*b* (the numeral "2" in a circle indicating a second step of insertion; e.g., press and lock of the other end of the cassette 102 within the pump 100). The flow direction indicia 412*c* indicates direction of fluid flow with a series of triangles formed in the external face 402 of the cassette housing 103*b*.

As described in further detail below, two cutout (cutouts 404*a* and 404*b*) correspond to respective lever arms 202*a* and 202*b* and two cutouts (cutouts 404*c* and 404*d*) correspond to respective positioning hooks 206*a* and 206*b*. The cutouts are sized and positioned to permit flexibility of the lever arms 202 and vertical side walls 109 during press-fit insertion of the free-flow prevention device 110, while retaining sufficient structural integrity of the cassette 102 for forcing fluid through a tube 108 within the cassette 102 using the peristaltic pump 106 of the ambulatory pump 100. In particular, the cutouts 404 in the walls of the cassette 102 permit inward movement of the lever arms 202 and outward bending of the vertical side walls 109 in the vicinity of the lever arms during press-fit insertion of the free-flow prevention device 110. In the illustrated example, cutouts 404*c* and 404*d* are rectangular and cutouts 404*a* and 404*b* each include a respective first rectangular region 406*a* and 406*b* and a respective second, smaller rectangular region 408*a* and 408*b*.

Figure 4B:
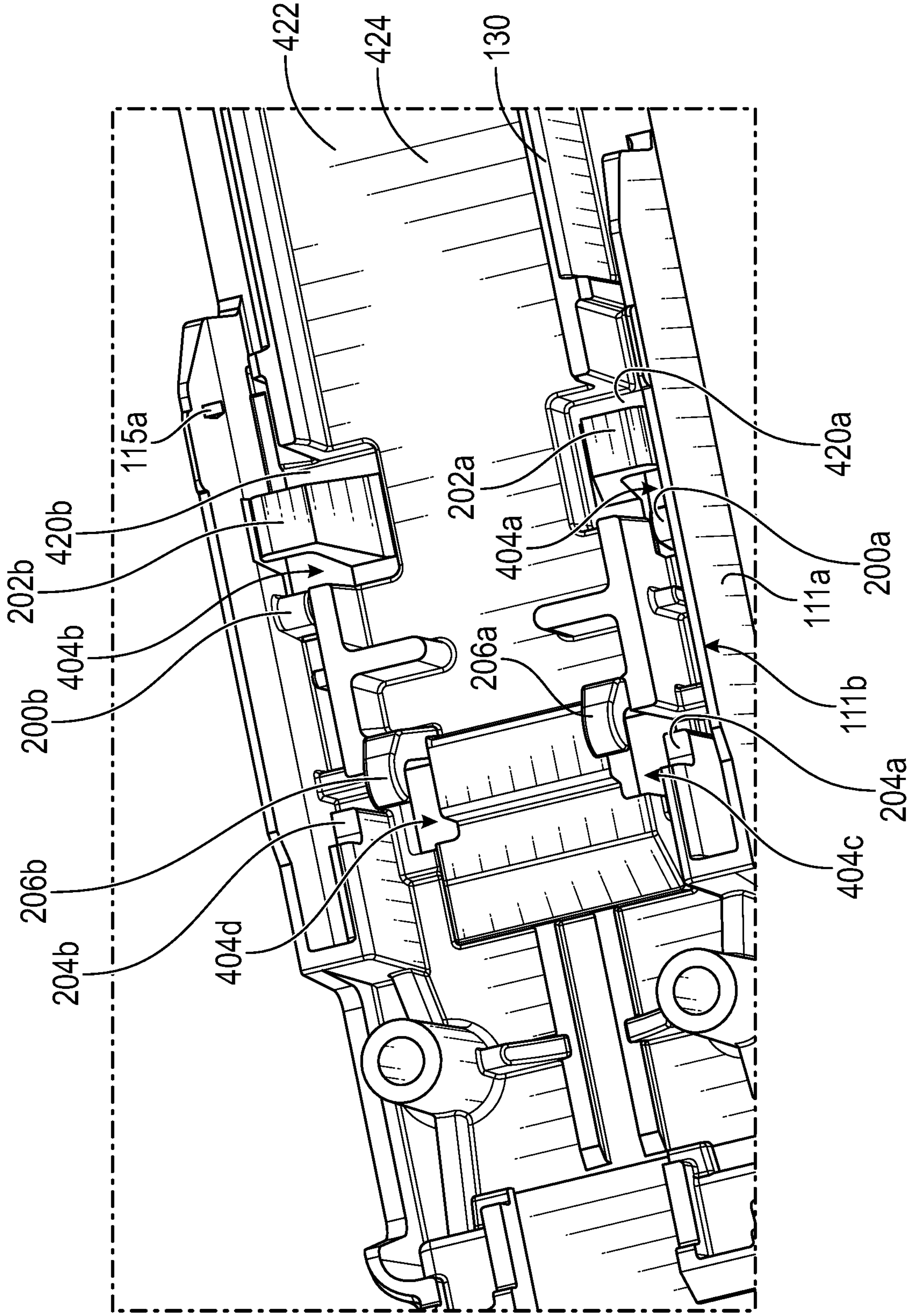
FIG. 4B is a bottom partial view of the cassette of FIG. 4A.
Figure 4C:
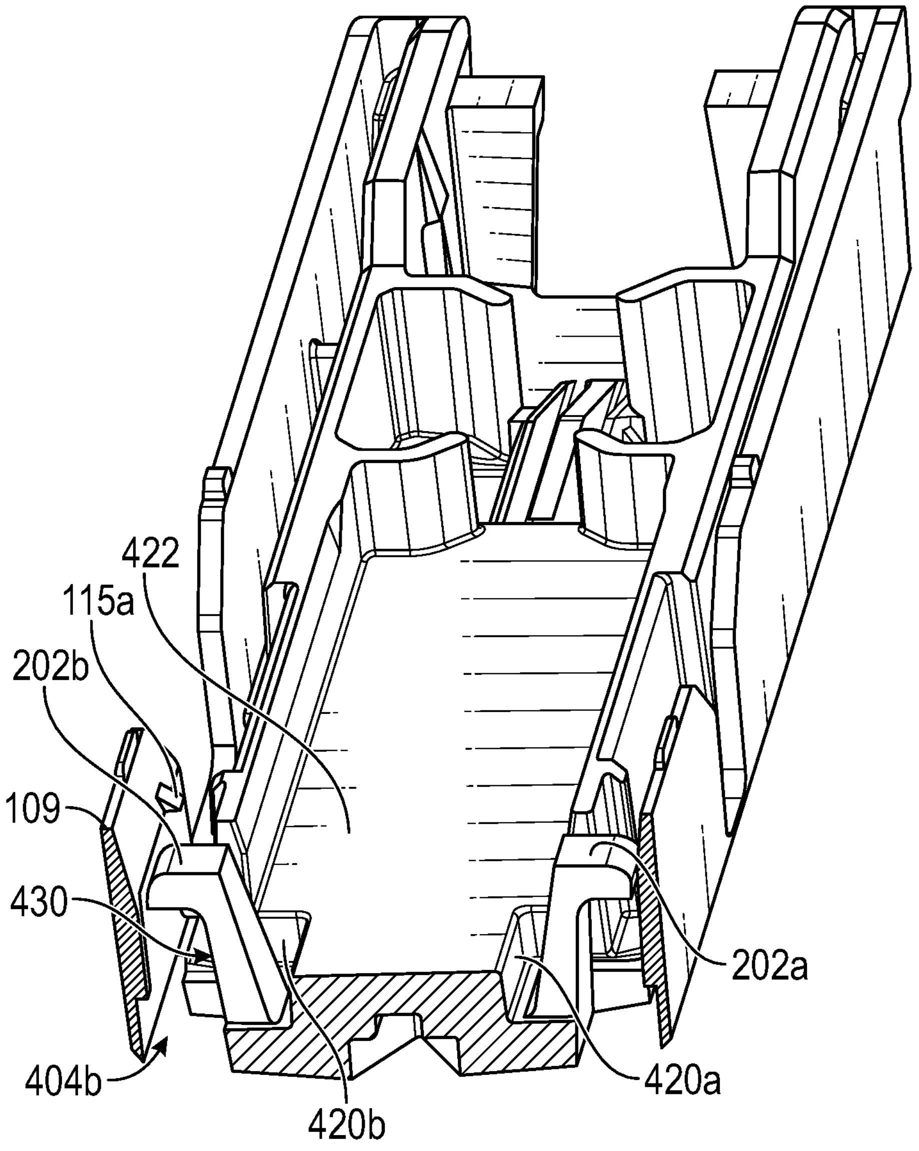
FIG. 4C is a perspective end cut away view of the cassette of FIG. 4A.

FIGS. 4B and 4C depicts a bottom view of the cassette 102 (i.e., the surface facing the pump 100 when inserted) in accordance with one example. The cassette 102 includes a press plate 422 that is coupled to the external face 402 (e.g., via ribs 410; FIG. 4A). The press plate 422 includes a channel 424 for receiving the tubing 108 (FIG. 1B). The press plate 422 along with the sidewalls 130 extending therefrom at least partially define the channel 424.

In the illustrated example, the cassette 102 includes a first well 420*a* in the press plate 422 surrounding the first lever arm 202*a* and a second well 420*b* in the press plate 422 surrounding the second lever arm 202*b*. The wells 420 facilitate inward bending of the respective lever arms 202 (in addition to bending permitted by the respective cutouts 404). In an alternative example, the first and second wells 420*a* and 420*b* may be omitted with the lever arms 202*a* and 202*b* integrated into the side walls 130 (see FIG. 2D). The size and location of the cutouts and wells, the thickness and chamfering of the vertical side walls 111, and the materials used can be adjusted to alter the insertion force needed to press-fit insert the free-flow prevention device 110 to facilitate manufacturing. It is contemplated that one or more of the cutouts 404, wells 420, or chamfering may be omitted if suitable insertion forces for the free-flow prevention device 110 are achieved with the remaining structures. In an example, the insertion force is between 100 and 400 newtons (e.g., between 140 newtons and 200 newtons).

FIG. 4C depicts a cut-away end view of the cassette 102 at the lever arms 202. The second lever arm 202*b* includes an angled extension 430 extending from the well 420*b* toward a vertical sidewall 109. The first lever arm 202*a* also includes an angled extension that is a mirror image of the angled extension 430. The angled extensions further permits inward bending of the respective lever arms 202 during press-fit insertion of the free-flow prevention device 110. In an example, the angled extensions have an angle of between 5 degrees and 20 degrees from perpendicular to the press plate 422.

Figure 4D:
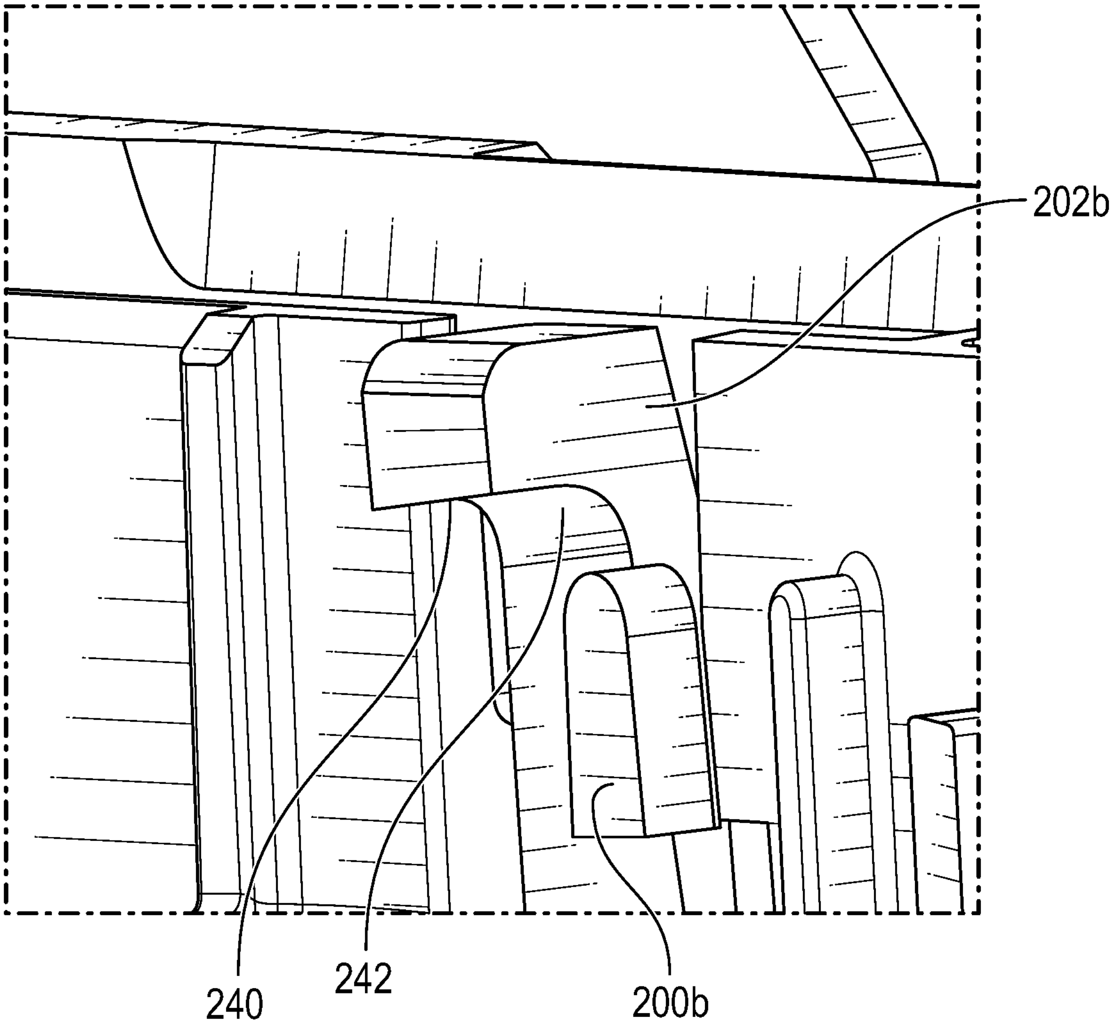
FIG. 4D is a perspective side cut away view of the cassette of FIG. 4A illustrating a lever arm.

FIG. 4D depicts a cut-away perspective view of the second lever arm 202*b* and a fulcrum 200*b*. The lever arm 202*b* includes an angled portion 240 that acts as an upper pivot point and the fulcrum 200*b* acts as a lower pivot point/support to permit rotational movement of the free-flow prevention device 110 (e.g., during insertion of the cassette 102 into the pump 100 or manual manipulation by an operator). The angled portion 240 additionally reduces stress on the free-flow prevention device during movement and distributes force across the face of the angled portion 240. In an example, the angled portion 240 has an angle of between 5 degrees and 20 degrees with respect to the press plate 422. The second lever arm 202*b* additionally includes a curved portion 242 between the angled extension 430 (FIG. 4C) and the angled portion to further reduce stress on the free-flow prevention device and the lever arms 202 202*a*, 202*b* during movement. The first lever arm 202*a* is a mirror image of the second lever arm 202*b*.

Figure 4E:
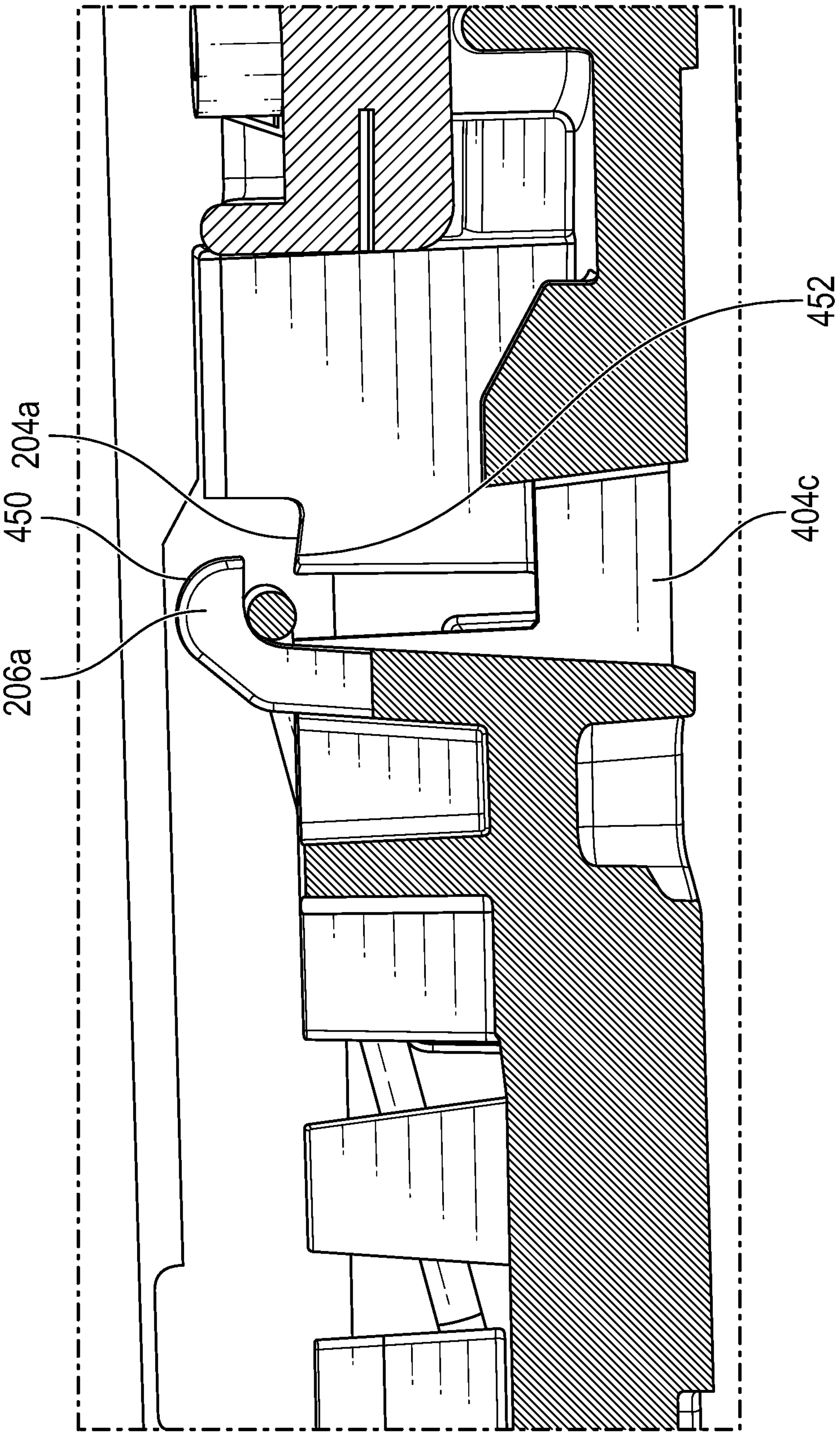
FIG. 4E is a side partial cut away view of the cassette of FIG. 4A illustrating a positioning hook.

FIG. 4E depicts a cut-away side view of the first positioning hook 206*a*. The first positioning hook 206*a* includes a curved guiding surface 450 to facilitate positioning of the free-flow prevention device 110 on the ledge 204*a*. Additionally, the ledge 204*a* has an angled surface 452 to facilitate positioning of the free-flow prevention device 110 on the ledge 204*a* and retaining the free-flow prevention device on the ledge until it is deliberately moved off the ledge by the wedge cams 116 (FIG. 2D). The cutout 404*c* adjacent the first hook 206*a* enables a mold tool to form the underside of the positioning hook and optionally may be configured to permit flexing of the positioning hook away from the ledge 204*a* during insertion of the free-flow prevention device. The second positioning hook 206*b* is the same or substantially similar to the first positioning hook 206*a* in construction and operation.

Figure 4F:
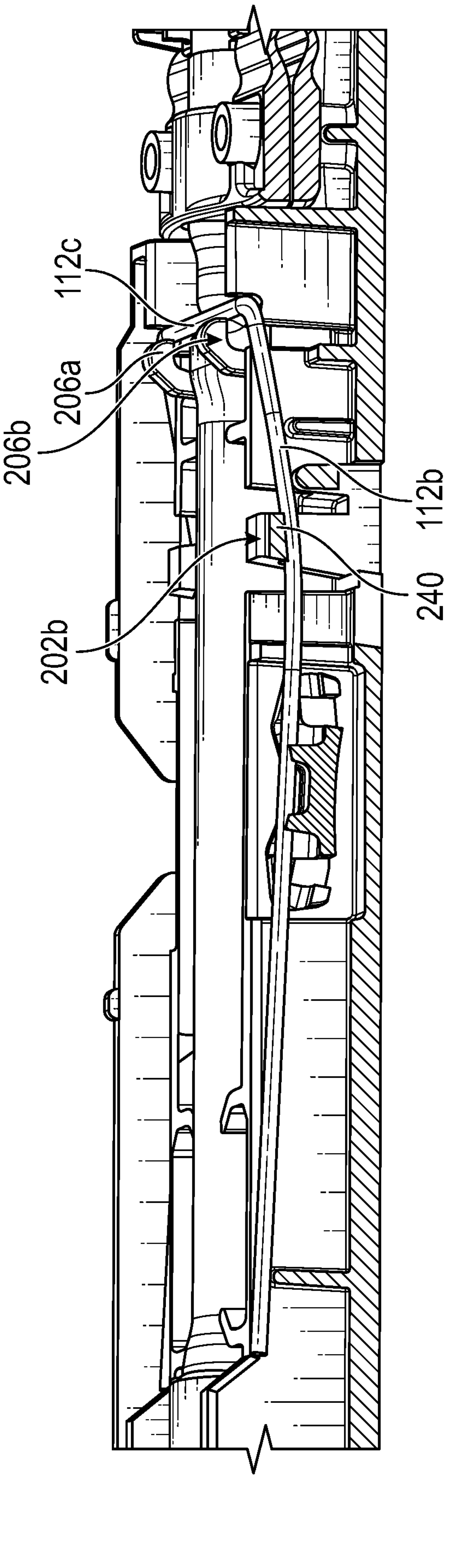
FIG. 4F is a side partial cut away view of the cassette of FIG. 4A illustrating positioning of the free-flow prevention device within the cassette.

FIG. 4F depicts a cutaway perspective view of the cassette with the free-flow prevention device 110 installed and in an open position prior to movement off the ledges 204 (e.g., in a shipping state). In this state, the second elongate portion 112*b* abuts the angled surface 240 of the second lever arm 202*b* (FIG. 4D), the first elongate portion 112*a* abuts the angled surface of the first lever arm (not shown), and the clamping section 112*c* is supported by the ledge 204 (FIGS. 2A and 4E) enabling fluid to flow through the tubing 108.

Figure 5:
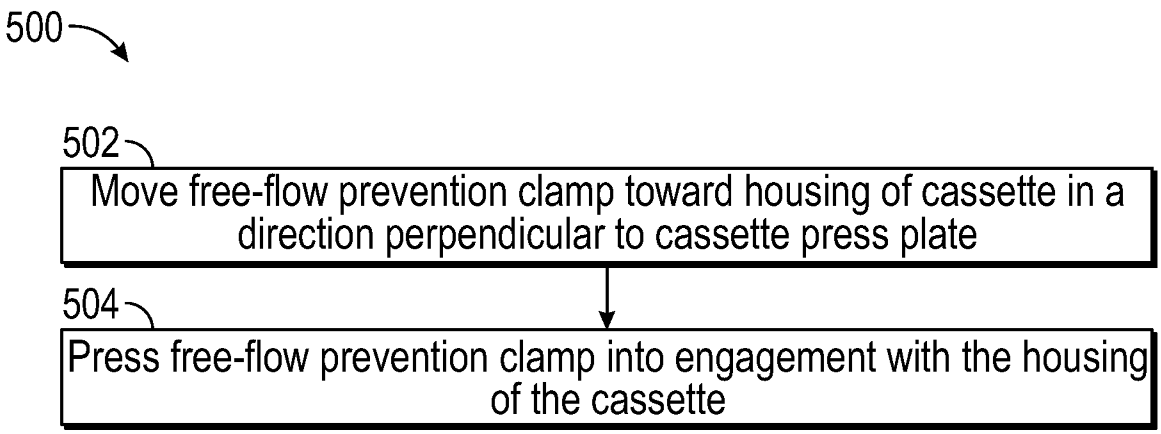
FIG. 5 is a flow chart of example steps for press-fit insertion of a free-flow prevention device.

FIG. 5 depicts a flowchart 500 of example steps of a manufacturing process for press-fit insertion of a free-flow prevention device into a housing of a cassette. Although the steps are described with reference to cassette 102 and free-flow prevention device 110, other suitable cassettes and free-flow prevention devices in which one or more steps of the flowchart 500 can be practiced will be understood by one of skill in the art from the description herein. Additionally, it is contemplated that one or more of the steps shown in FIG. 5, and described herein, may be omitted, performed simultaneously or in series, performed in an order other than illustrated and described, or performed in conjunction with additional steps.

At block 502, move the free-flow prevention device 110 toward a housing 103*b* of the cassette 102. In an example, the free-flow prevention device 110 is moved in a direction perpendicular to the press plate 422 of the cassette housing 103*b*. The free-flow prevention device may be moved manually or using production apparatus. The production apparatus may be a robotic assembly system including a support configured to support the cassette housing 103*b* in a predefined orientation and a robotic arm configured to grasp, manipulate, and move the free-flow prevention device 110 toward the cassette housing 103*b*. A processor of the robotic assembly system is programmed with instructions for moving the robotic arm relative to the support in order to move the free-flow prevention device 110 toward the cassette housing 103*b*. Other suitable production apparatus will be understood by one of skill in the art from the description herein.

At block 504, press the free-flow prevention device 110 into engagement with the housing 103*b* of the cassette 102. The free-flow prevention device may be pressed into engagement manually or using production apparatus.

Wherein production apparatus is used, the processor of the robotic assembly system is further programmed with instructions for moving the robotic arm such that the free-flow prevention device 110 is moved into engagement with the housing with a predefined insertion force that overcomes resistance encountered by the free-flow prevention device due to one or more of the lever arms, vertical sidewalls, and positioning hooks.

In an example, the housing 103*b* includes an external face 402, a press plate 422 coupled to the external face 402 (e.g., by ribs 410), a first lever arm 202*a* spaced from a first vertical sidewall 109 extending from the external face 402, and a second lever arm 202*b* spaced from a second vertical sidewall 109 extending from the external face 402. The first elongate section 112*a* contacts the first lever arm 202*a* and the first vertical sidewall 109 and the second elongate section 112*b* contacts the second lever arm 202*b* and the second sidewall 109 as the free-flow prevention device 110 is pressed into engagement with the housing 103*b*. The housing 103*b* includes cutouts 404 in the external face 402 adjacent the first and second vertical sidewalls 109 and the first and second lever arms 202 that permit outward bending of the first and second vertical side walls and inward movement of the first and second lever arms due to the cutouts in the walls of the cassette 102 to allow the respective first and second elongate sections to pass while pressing the free-flow prevention device into engagement with the housing.

The terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A cassette with free-flow prevention that is insertable into an infusion pump having a peristaltic actuator, the cassette comprising:

a free-flow prevention device including a clamping section having a first side and a second side, a first elongate section extending from the first side, and a second elongate section extending from the second side; and a housing configured to receive and support the free-flow prevention device, the housing defining a channel for receiving a tube, the first elongate section and the second elongate section of the free-flow prevention device, when received, extending parallel to the channel and the clamping section extending across the channel, the housing comprising:

an external face;

a press plate coupled to the external face;

a lever arm retention system configured to retain the free-flow prevention device when received, the lever arm retention system including a first lever arm configured to engage the first elongate section and a second lever arm configured to engage the second elongate section;

vertical sidewalls extending from the external face, the vertical sidewalls including a first vertical sidewall spaced from the first lever arm and a second vertical sidewall spaced from the second lever arm, wherein the first vertical sidewall is chamfered in a first region corresponding to the first lever arm and the second vertical sidewall is chamfered in a second region corresponding to the second lever arm; and cutouts in the external face adjacent the first and second vertical sidewalls that permit outward bending of the first and second vertical side walls during press-fit insertion of the free-flow prevention device in a direction perpendicular to the press plate.

2. The cassette of claim 1, further comprising:

a first channel wall extending from the press plate that at least partially defines the channel, the first lever arm integrated into the first channel wall; and a second channel wall extending from the press plate that at least partially further defines the channel, the second lever arm integrated into the second channel wall.

3. The cassette of claim 1, wherein the first lever arm comprises a first retaining surface facing the first elongate section and the second lever arm comprises a second retaining surface facing the second elongate section to retain the free-flow prevention device after insertion.

4. The cassette of claim 3, further comprising:

a plurality of supports positioned to support the first and second elongate sections when the free-flow prevention device is received;

wherein the first and second retaining surfaces are each angled and curved to permit rotational movement of the respective first and second elongate sections about a respective one of the plurality of supports.

5. The cassette of claim 4, wherein an angle of each of the first and second retaining surfaces is between 5 degrees and 20 degrees with respect to the press plate.

6. The cassette of claim 4, wherein each of the respective one of the plurality of supports is adjacent a respective one of the cutouts.

7. The cassette of claim 1, further comprising:
- a first positioning hook and a second positioning hook extending away from the press plate, each positioning hook having a surface configured to engage the clamping section during insertion to assist in positioning the free-flow prevention device.

8. An infusion system, the system comprising:
- an infusion pump having a peristaltic actuator, and the cassette with free-flow prevention of claim 1.

9. A method for manufacturing a cassette with free-flow prevention, the cassette configured for insertion into an infusion pump, the method comprising:
- moving a free-flow prevention device toward a housing of the cassette in a direction perpendicular to a press plate of the cassette, the free-flow prevention device including a clamping section having a first side and a second side, a first elongate section extending from the first side, and a second elongate section extending from the second side, and
- pressing the free-flow prevention device into engagement with a housing of the cassette, the housing including an external face, an external face coupled to the press plate, a first lever arm spaced from a first vertical sidewall extending from the external face and a second lever arm spaced from a second vertical sidewall extending from the external face, wherein the first vertical sidewall is chamfered in a first region corresponding to the first lever arm and the second vertical sidewall is chamfered in a second region corresponding to the second lever arm, the first elongate section contacting the first lever arm and the first vertical sidewall and the second elongate section contacting the second lever arm and the second sidewall during the pressing into engagement, the housing further including cutouts in the external face adjacent the first and second vertical sidewalls that permit outward bending of the first and second vertical side walls to allow the respective first and second elongate sections to pass while pressing the free-flow prevention device into engagement with the housing.

10. The method of claim 9, the housing further comprising a first channel wall extending from the press plate that at least partially defines the channel, the first lever arm integrated into the first channel wall; and a second channel wall extending from the press plate that at least partially further defines the channel, the second lever arm integrated into the second channel wall.

11. The method of claim 9, wherein the first lever arm comprises a first retaining surface facing the first elongate section and the second lever arm comprises a second retaining surface facing the second elongate section to retain the free-flow prevention device after the pressing into engagement.

12. The method of claim 11, the housing further comprising a plurality of supports positioned to support the first and second elongate sections after the pressing into engagement;
- wherein the first and second retaining surfaces are each angled and curved to permit rotational movement of the respective first and second elongate sections about a respective one of the plurality of supports.

13. The method of claim 12, wherein an angle of each of the first and second retaining surfaces is between 5 degrees and 20 degrees with respect to the press plate.

14. The method of claim 12, wherein each of the respective one of the plurality of supports is adjacent a respective one of the cutouts.

15. The method of claim 9, the housing further comprising a first positioning hook and a second positioning hook extending away from the press plate, each positioning hook having a surface configured to engage the clamping section during insertion to assist in positioning the free-flow prevention device.

* * * * *